United States Patent [19]
Coffey et al.

[11] 4,339,596
[45] Jul. 13, 1982

[54] TREATMENT OF BYPRODUCT STREAM FROM ADIPIC ACID MANUFACTURE

[75] Inventors: Freylon B. Coffey; Norbert F. Cywinski, both of Odessa, Tex.

[73] Assignee: El Paso Products Company, Odessa, Tex.

[21] Appl. No.: 94,425

[22] Filed: Nov. 15, 1979

[51] Int. Cl.³ .................... B01D 3/34; C07C 67/08
[52] U.S. Cl. .................. 560/204; 159/47 R; 203/6; 203/15; 210/806; 560/191; 562/513; 562/593
[58] Field of Search ..................... 560/204, 191; 203/14–16, 66, 38, 39, 43, 6; 210/21, 73, 806; 159/47 R, 48 L; 562/513, 593

[56] References Cited

U.S. PATENT DOCUMENTS

| | | | |
|---|---|---|---|
| 2,824,122 | 2/1958 | Kuceski | 560/204 |
| 3,726,888 | 4/1973 | Hatten et al. | 560/204 |
| 3,810,937 | 5/1974 | Kuceski | 560/204 |
| 3,886,199 | 5/1975 | Suter et al. | 560/204 |
| 4,052,441 | 10/1977 | Brunner | 560/204 |
| 4,076,948 | 2/1978 | Mims | 560/204 |
| 4,082,788 | 4/1978 | Mims | 560/204 |
| 4,105,856 | 8/1978 | Newton | 560/204 |

*Primary Examiner*—Wilbur L. Bascomb, Jr.
*Attorney, Agent, or Firm*—DePaoli & O'Brien

[57] ABSTRACT

In one embodiment, this invention provides a process for converting a dilute aqueous filtrate byproduct stream from adipic acid manufacture into a concentrated methanolic solution which does not solidify at ambient temperatures.

In another embodiment, this invention provides an improved process for the separation and recovery of byproducts associated with the isolation of $C_4$–$C_6$ dicarboxylic acids contained in a waste byproduct stream derived from an adipic acid manufacturing operation involving nitric acid oxidation of a cyclohexanone/cyclohexanol feedstream in the presence of a catalyst.

3 Claims, 1 Drawing Figure

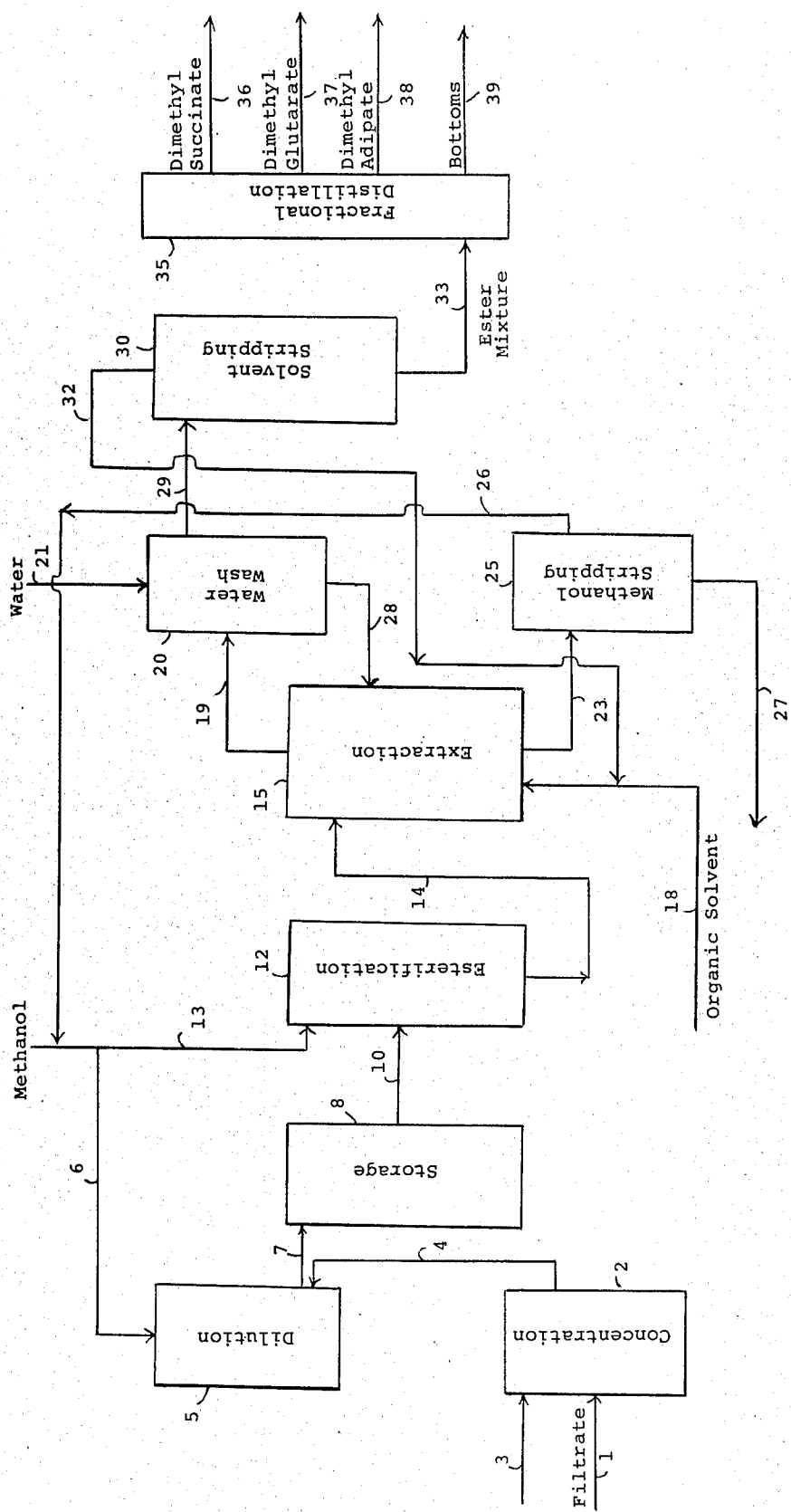

TREATMENT OF BYPRODUCT STREAM FROM ADIPIC ACID MANUFACTURE

BACKGROUND OF THE INVENTION

Commercial methods for producing dicarboxylic acids generally involve oxidizing naphthenes, cycloaliphatic ketones or cycloaliphatic alcohols with nitric acid in the presence of metal oxidation catalysts.

In the case of adipic acid, specific feed materials such as cyclohexane, cyclohexanone and/or cyclohexanol in admixture with nitric acid are heated at about 40°–140° C. in the presence of a catalyst. The resultant oxidation reaction product comprises adipic acid together with small amounts of monocarboxylic acids and dicarboxylic acids and other organic components in admixture with nitric acid and catalyst components. A substantial quantity of the adipic acid product is recovered by cooling the solution and filtering off the crystallized adipic acid. Oxidation methods of adipic acid production are described in U.S. Pat. Nos. 2,439,513; 2,557,281; 2,719,566; 2,840,607; 2,971,010; 3,338,959; and references cited therein.

In a process involving nitric acid oxidation of cyclohexanone and/or cyclohexanol, economically significant amounts of succinic acid and glutaric acid are formed as byproducts in admixture with the adipic acid. After the major portion of the adipic acid is separated by crystallization and filtration, the aqueous filtrate mother liquor contains some adipic acid, as well as succinic acid, glutaric acid, nitric acid and metal catalyst values.

Usually this filtrate has been treated as a waste stream. Because of environmental and economic considerations, there has been continuing research effort to develop methods for recovering the valuable and reusable organic and inorganic components of the said waste filtrate byproduct stream.

U.S. Pat. No. 3,726,888 describes a process for the separation and recovery of the components contained in the filtrate byproduct stream of an adipic acid manufacturing plant. The filtrate stream comprises an aqueous solution of adipic acid, glutaric acid, succinic acid, metal catalyst values and nitric acid. The separation and recovery process involves contacting the filtrate with alkanol, and extracting with a water-immiscible organic solvent to provide an organic phase containing the formed esters, and to provide an aqueous phase containing the nitric acid and metal catalyst values. Each of the phases is fractionated to separate the mixtures into useful components.

U.S. Pat. Nos. 4,076,948 and 4,082,788 describe processing improvement which are adapted to overcome some of the difficulties characteristic of the byproduct separation and recovery technology disclosed in the above recited U.S. Pat. No. 3,726,888.

Among the problems encountered during the handling and treatment of the described filtrate byproduct stream from adipic acid manufacture is the fact that the said filtrate byproduct stream contains a relatively high water content. If the filtrate byproduct stream is concentrated by vacuum distillation to reduce the water content, the resultant concentrate solution solidifies at ambient temperatures. Consequently, it is then necessary to maintain the temperature of the concentrate solution at a temperature above about 75° C. during storage or shipping in order to prevent the concentrated solution from solidifying. For example, large volume shipments require the use of tankcars equipped with heating coils.

There remains a need for improvements in the technology relating to the handling and treatment of a dilute aqueous filtrate byproduct stream which is a waste effluent from an adipic acid manufacturing plant.

Accordingly, it is an object of this invention to provide a method for improving the economics of handling and treating a waste effluent from an adipic acid manufacturing plant.

It is another object of this invention to provide a process for converting a dilute aqueous filtrate byproduct stream from adipic acid manufacture into a concentrate solution which does not solidify at ambient temperatures.

It is a further object of this invention to provide an improved process for the separation and recovery of dicarboxylic acids and other valuable components contained in a filtrate byproduct stream derived from an adipic acid manufacturing operation, which operation involves nitric acid oxidation of cyclohexanone and/or cyclohexanol.

Other objects and advantages of the present invention shall become apparent from the accompanying description and Example.

BACKGROUND OF THE INVENTION

As noted previously, in the oxidation of cyclohexanone and/or cyclohexanol with nitric acid in the presence of a metal oxidation catalyst, the resulting oxidation product solution is processed for recovery of the bulk of the desired adipic acid by crystallization and filtration. The acidic mother liquor (i.e., the aqueous filtrate byproduct stream) contains quantities of monobasic and dibasic carboxylic acids as well as nitric acid and metal catalyst values.

A typical filtrate byproduct stream nominally corresponds to the following weight percent composition:

| Component | Amount |
|---|---|
| Succinic acid | 3–10% |
| Glutaric acid | 3–35% |
| Adipic acid | 3–6% |
| Nitric acid | 6–20% |
| Catalyst | 1–3% |
| Water | Balance |

The catalyst values contained in the filtrate are those which are conventionally employed in cyclohexanone/cyclohexanol oxidation procedures, such as copper, vanadium, and the like.

One or more objects of the present invention are accomplished by the provision of a method of facilitating the storage and transport of an aqueous waste byproduct stream derived from a process for producing adipic acid by nitric acid oxidation of cyclohexanone/cyclohexanol, which method comprises the steps of (1) concentrating the volume of the aqueous filtrate medium by the removal of water and the volatile components which co-distill with water to provide a concentrate solution which has a water content between about 5–30 weight percent and a nitric acid content between 1–6 weight percent, based on total solution weight; and (2) admixing the concentrate solution with between about 5–20 weight percent methanol, based on total solution weight, to form a single phase homogeneous solution; wherein the said homogeneous solution has a freezing point below about 5° C.

In another embodiment, this invention provides a method of facilitating the storage and transport of an aqueous waste byproduct stream derived from a process for producing adipic acid by nitric acid oxidation of cyclohexanone/cyclohexanol, which method comprises the steps of (1) concentrating the volume of the aqueous filtrate medium by the removal of water and the volatile components which co-distill with water to provide a concentrate solution which has a water content between about 5-30 weight percent and a nitric acid content between about 1-6 weight percent, based on total solution weight; (2) admixing the concentrate solution with between about 5-20 weight percent methanol, based on total solution weight; and (3) heating the admixture at a temperature in the range between about 35°-60° C. for a period of time between about 5-45 minutes sufficient to form a single phase homogeneous solution and to effect partial esterification of the $C_4$-$C_6$ carboxylic acid components contained in the homogeneous solution; wherein the said homogeneous solution has a freezing point below about 0° C.

The intermediate concentrate solution provided by step (1) of the process on the average contains between about 50-70 weight percent, based on solution weight, of a mixture of succinic acid, glutaric acid and adipic acid.

The single phase homogeneous solution which is obtained as the product of the process embodiments described above is characterized by a freezing point which is below about 5° C., and which normally is below about 0° C.

The low freezing point property of the homogeneous solution is the result of two contributing factors. First, the monomethyl esters and dimethyl esters of the dicarboxylic acid components have a lower freezing point than the free acid form of the corresponding dicarboxylic acids. Second, the presence of the methanol, monoester and diester components enhance the overall solvation effect, and there is a concomitant increased miscibility between the solution components.

An important advantage of a low freezing point solution is the fact that the solution remains in liquid form at ambient temperature during any subsequent handling operation such as storage or shipment, particularly when the handling operation is a prelude to further processing such as byproduct recovery.

In a further embodiment, the present invention contemplates an improved method for producing dimethyl esters of $C_4$-$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5-30 weight percent and a nitric acid content between 1-6 weight percent, based on total solution weight; (2) admixing the concentrate solution with between about 5-20 weight percent methanol, based on total solution weight, to form a single phase homogeneous solution; wherein the said homogeneous solution has a freezing point below about 5° C.; and after a transitional storage and/or shipment stage, performing additional processing steps which comprise (a) admixing the homogeneous solution product of step (2) with a quantity of methanol to provide a total of between about 25-60 weight percent methanol, based on solution weight, and heating the solution at a temperature between about 60°-90° C. to form methyl esters of the $C_4$-$C_6$ carboxylic acid components; (b) extracting the methyl ester components by contacting the esterification medium with a water-immiscible organic solvent at a temperature between about 40°-90° C.; (c) separating the immiscible organic solvent phase and aqueous phase; (d) fractionally distilling the organic solvent phase to recover a refined mixed dimethyl ester fraction; and (e) concentrating the aqueous phase by distillation to provide a residual aqueous solution containing nitric acid and metal catalyst values.

An important aspect of the present invention process embodiments is the step (1) concentration of the volume of the aqueous filtrate medium by the removal of water and nitric acid, and other volatile components which co-distill with water. The volatile components which co-distill with the water and nitric acid include butyric acid, valeric acid and caproic acid.

Several advantages derive from the step (1) concentration of the aqueous filtrate byproduct stream.

First, the reduced volume of the filtrate medium permits the use of smaller capacity equipment for any subsequent esterification and extraction steps of the process.

Second, the reduced proportion of water in the filtrate concentration solution causes a favorable equilibrium shift toward ester formation in the esterification reaction between carboxylic acid byproducts and methanol.

Third, the removal of monobasic acids during the step (1) concentration of the filtrate byproduct stream facilitates the production and recovery of byproduct dimethyl esters having improved color and odor specifications.

Fourth, the removal of nitric acid during the step (1) concentration of the filtrate byproduct stream has the important advantage of reducing the level of methyl nitrite and methyl nitrate byproduct formation during the subsequent esterification reaction phase. The formation of these byproducts is primarily a function of the nitric acid concentration. These byproducts are undesirable because they cause the loss of both methanol and nitric acid. Further, these byproducts tend to be unstable and represent a potential explosion hazard. They must be purged periodically from the process system.

Fifth, the recovery of nitric acid during the step (1) concentration phase permits a highly efficient recycle of the said nitric acid to the cyclohexanone/cyclohexanol oxidation system.

With reference to step (a) of the process embodiment described above, a unique feature of the esterification reaction at 60°-90° C. is the rate efficiency with which equilibrium is achieved between the esterified and unesterified dicarboxylic acid components, even in the presence of a highly dilute aqueous nitric acid solution. The efficiency of the step (a) esterification reaction is attributable to a combination of determining factors, such as an elevated reaction temperature, a high proportion of methanol relative to a low proportion of water, the absence of interfering byproduct components (e.g., monocarboxylic acids), and the like.

The step (a) esterification reaction time on the average will vary in the range between about 5-25 minutes, depending on the temperature maintained in the esterification zone.

In a similar manner, the combination of selected conditions of the step (b) extraction stage of the process embodiment provides technical advantages. Hence, an extraction temperature in the range between about 40°–90° C. has the beneficial effect of accelerating the additional conversion of free carboxylic acids to methyl ester derivatives. Substantially complete transfer of dimethyl esters into the organic solvent is achieved during the step (b) extraction period. This efficient extraction of dimethyl esters by the organic solvent is readily accomplished within a phase contact period between about 2–20 minutes.

The quantity of water-immiscible organic solvent employed in the step (b) extraction stage of the invention process usually will vary in the range between about 0.5–2 volumes per volume of esterification medium being extracted, and on the average will approximate a volume ratio of 1:1.

A preferred type of water-immiscible organic solvent is one selected from aromatic hydrocarbons, aliphatic hydrocarbons, cycloaliphatic hydrocarbons, halogenated aliphatic hydrocarbons and halogenated aromatic hydrocarbons. Particularly preferred species include cyclohexane, benzene, toluene, xylene, ethylbenzene, chloroform, o-dichlorobenzene, and the like.

Because of the elevated temperature up to 90° C. employed during the esterification and extraction steps of the invention process, equipment is employed which is adapted for 15–200 psi reaction systems. The process embodiments can be conducted either batchwise or continuously.

At the end of the step (b) extraction period, the immiscible organic solvent and aqueous phases are separated and individually recovered for subsequent manipulative procedures.

In a particularly preferred embodiment, the organic solvent phase is contacted with wash water in a manner sufficient to remove substantially all of the methanol and residual nitric acid components present in the organic solvent phase, and to reduce the free carboxylic acids and monomethyl esters of dicarboxylic acids content of the organic solvent phase. The water washing step facilitates the subsequent recovery of high quality organic byproducts.

The said organic solvent phase can be distilled to strip the solvent medium, and yield a refined mixed dimethyl ester fraction. The said ester mixture can be employed directly to prepare high molecular weight esters applicable as plasticizers for polyvinyl chlorides. Alternatively, the ester mixture can be further fractionated to yield pure dimethyl succinate, dimethyl glutarate and dimethyl adipate, respectively. If desired, the dimethyl esters can be hydrolyzed to the corresponding high purity acids.

With respect to the aqueous phase which is separated and recovered after the step (b) extraction operation, preferably the said aqueous phase is subjected to concentration in vacuo to remove the dissolved methanol content and to provide a residual aqueous solution containing nitric acid and copper/vanadium type metal values. The said residual aqueous solution is suitable for recycle to the cyclohexanone/cyclohexanol oxidation system.

The practice of the present invention as a continuous process can be better understood by reference to the accompanying drawing which is illustrated as a flow diagram.

In the drawing, a filtrate stream is fed through line 1 into Concentration unit 2. Nitric acid, monocarboxylic acids and other volatile components which co-distill with water are removed through line 3. A concentrate solution of reduced water and nitric acid content is recovered from Concentration unit 2 as a liquid phase, and passed through line 4 into Dilution unit 5. Methanol is entered into Dilution unit 5 via line 6, and the dilution admixture is stirred at a temperature of 40° C. for a period of about 10 minutes to form a homogeneous solution. The homogeneous solution is passed via line 7 to Storage unit 8.

Subsequently, the homogeneous solution is withdrawn from the Storage unit and fed through line 10 into Esterification unit 12. Methanol is entered into Esterification unit 12 through line 13, and the esterification reaction is conducted at a temperature of about 70° C. for a period of about 20 minutes to form methyl esters of $C_4$–$C_6$ carboxylic acids.

The esterification reaction medium is withdrawn continuously from Esterification unit 12 through line 14 and introduced into Extraction unit 15. An organic solvent (e.g., benzene) is fed countercurrently into Extraction unit 15 by means of line 18. The extraction cycle is conducted at a temperature of 70° C. for a contact time of about 5 minutes. The organic solvent phase is recovered from Extraction unit 15 and passed through line 19 into Water Wash unit 20, and there it is contacted countercurrently with water which is fed through line 21 into Water Wash unit 20. The aqueous phase is recovered from Extraction unit 15 and passed through line 23 into Methanol Stripping unit 25. The stripped methanol is recycled to Exterification unit 12 through line 26, and the residual aqueous nitric acid solution and the metal catalyst values contained therein from Methanol Stripping unit 25 is recycled to the adipic acid production unit through line 27.

The spent water wash stream from Water Wash unit 20 is recycled through line 28 to Extraction unit 15. The washed organic solvent stream is recovered from Water Wash unit 20 and passed through line 29 into Solvent Stripping unit 30. The stripped organic solvent is recycled to Extraction unit 15 via line 32. A mixed dimethyl ester fraction is withdrawn from Solvent Stripping unit 30 through line 33, and charged to Fractional Distillation unit 35. Lines 36, 37, 38 and 39 are employed to isolate the dimethyl succinate, dimethyl glutarate, dimethyl adipate and bottoms fractions, respectively.

The following example is further illustrative of the present invention. The reactants and other specific ingredients are presented as being typical, and various modifications can be derived in view of the foregoing disclosure within the scope of the invention.

EXAMPLE

A quantity of an aqueous mother liquor from an adipic acid manufacturing plant is concentrated in vacuo to reduce the water content to about 20 weight percent and the nitric acid content to about 5 weight percent.

The concentrate solution contains about 16.5 weight percent succinic acid, 43.9 percent glutaric acid and 8 weight percent adipic acid. The concentrate solution has a freezing point of about 75° C.

A sample of the concentrate solution is admixed with about 5 weight percent of methanol, based on the total weight of the concentrate solution, and the admixture is stirred at 50° C. until a clear single phase solution is obtained. The solution is allowed to stand for a period of about 24 hours at 40° C. Under these conditions a small amount of crystalline solid separates from the solution.

A second sample of the concentrate solution is admixed with about 10 weight percent of methanol, based on the total weight of the concentrate solution, and the admixture is stirred at 50° C. until a clear single phase solution is obtained. There is no formation of solid precipitate when the solution is cooled to room temperature, or when the solution is maintained at a temperature of about 4° C. for a period of about 24 hours.

In the same manner, a sample of concentrate solution is diluted with about 15 weight percent of methanol. There is no formation of solid precipitate phase when the solution is cooled to 4° C., or when the solution stands at ambient temperatures for an extended period of time, e.g., one month or more at outdoor temperatures.

What is claimed is:

1. A method of facilitating the storage and transport of an aqueous filtrate waste byproduct stream derived from a process for producing adipic acid by nitric acid oxidation of cyclohexanone/cyclohexanol, which method comprises the steps of (1) reducing the volume of the aqueous filtrate medium by the removal of water and volatile components which co-distill with water to provide a concentrate solution which has a water content between about 5-30 weight percent and a nitric acid content between 1-6 weight percent, based on total solution weight; and (2) admixing the concentrate solution with between about 5-20 weight percent methanol, based on total solution weight, to form a single phase homogeneous solution; wherein the said homogeneous solution has a freezing point below about 5° C.

2. A method of facilitating the storage and transport of an aqueous filtrate byproduct stream derived from a process for producing adipic acid by nitric acid oxidation of cyclohexanone/cyclohexanol, which method comprises the steps of (1) reducing the volume of the aqueous filtrate medium by the removal of water and volatile components which co-distill with water to provide a concentrate solution which has a water content between about 5-30 weight percent and a nitric acid content between about 1-6 weight percent, based on total solution weight; (2) admixing the concentrate solution with between about 5-20 weight percent methanol, based on total solution weight; and (3) heating the admixture at a temperature in the range between about 35°-60° C. for a period of time between about 5-45 minutes sufficient to form a single phase homogeneous solution and to effect partial esterification of the $C_4$-$C_6$ carboxylic acid components contained in the homogeneous solution; wherein the said homogeneous solution has a freezing point below about 0° C.

3. A method in accordance with claim 2 wherein the step (2) concentrate solution contains between about 50-70 weight percent, based on solution weight, of a mixture of succinic acid, glutaric acid and adipic acid.

* * * * *